US008080519B2

(12) United States Patent
Zimmer

(10) Patent No.: US 8,080,519 B2
(45) Date of Patent: Dec. 20, 2011

(54) COMPOSITIONS AND METHODS FOR ENHANCED PHARMACOLOGICAL ACTIVITY OF COMPOSITIONS COMPRISING PEPTIDE DRUG SUBSTANCES

(75) Inventor: Robert H. Zimmer, Mulhouse Cedex (FR)

(73) Assignee: ImmuPharma SA (France) (FR)

( * ) Notice: Subject to any disclaimer, the term of this patent is extended or adjusted under 35 U.S.C. 154(b) by 0 days.

(21) Appl. No.: 12/687,982

(22) Filed: Jan. 15, 2010

(65) Prior Publication Data

US 2010/0292158 A1 Nov. 18, 2010

Related U.S. Application Data

(60) Division of application No. 10/825,472, filed on Apr. 15, 2004, now Pat. No. 7,671,029, which is a continuation of application No. 10/237,254, filed on Sep. 6, 2002, now abandoned, and a continuation of application No. 10/050,903, filed on Jan. 16, 2002, now Pat. No. 6,908,900, and a continuation of application No. 09/844,426, filed on Aug. 7, 2000, now abandoned.

(60) Provisional application No. 60/332,636, filed on Nov. 6, 2001, provisional application No. 60/317,737, filed on Sep. 6, 2001, provisional application No. 60/287,872, filed on May 1, 2001, provisional application No. 60/287,886, filed on May 1, 2001, provisional application No. 60/262,337, filed on Jan. 17, 2001, provisional application No. 60/147,749, filed on Aug. 6, 1999.

(51) Int. Cl.
*A61K 38/18* (2006.01)

(52) U.S. Cl. ...... 514/1.1; 514/18.5; 514/18.3; 514/21.3; 530/345

(58) Field of Classification Search ........................ None
See application file for complete search history.

(56) References Cited

U.S. PATENT DOCUMENTS 4,239,754 A 12/1980 Sache
4,336,534 A 6/1982 Kumagai
4,339,534 A 7/1982 Johansen
4,396,606 A 8/1983 Goldstein
4,694,006 A 9/1987 Bundgaard
4,925,673 A 5/1990 Steiner
4,335,119 A 7/1992 Johnsen et al.
5,212,158 A 5/1993 Fiez Vandai
5,624,894 A 4/1997 Bodor
6,136,952 A 10/2000 Li
6,908,900 B2 6/2005 Zimmer
7,671,029 B2 3/2010 Zimmer
2002/0090603 A1 7/2002 Lipton
2003/0060413 A1 3/2003 Zimmer
2004/0186058 A1 9/2004 Zimmer

FOREIGN PATENT DOCUMENTS

WO WO 98/11126 3/1998

OTHER PUBLICATIONS

Bernatowicz et al., *J. Med. Chem.* 39:4879-87 (1996).
Fukushima, K. *J. Med. Sci.* v71(6):727-43 (1996).
Vergnolle, N., et al. *P.N.A.S.* v95:7766-71 (1998).
Langguth, P., et al. *J. Controlled Release* v46(1):39-57 (1997).
Egleton, R.D., et al. *Brain Res.* v881(1):37-46 (2000).
Pauletti, G.M., et al. *Adv. Drug Deliv. Rev.* v27(2-3):235-56 (1997).
Ahlers et al. *P.N.A.S.* v94:10856-61 (1997).
Greenstein et al. *J. Immunol.* v148:3970-77 (1992).
Belyakov et al. *J. Clin. Investig.* v102(12):2072-81 (1998).
Patel et al. *FEBS lett.* v62(1):60-63 (1976).
Hashimoto et al. *Endocrinol.* v26(1):103-109 (1979).
Belyakov, et al., *Proc. Natl Acad. Sci. USA*, 1998, 95(4):1709-14.
Fukushima, K., Hypoglycemic Effect and Enhanced Gastrointestinal Absorption of Insulin Using New Cinnamoyl-phenylalanine Derivatives, Hokkaido Journal of Medical Science, vol. 71, No. 6, 1996, pp. 727-743.
Vergnolle, N., et al., Proteinase-Activated Receptor 2 ($PAR_2$)-Activating Peptides: Identification of A Receptor Distinct From $PAR_2$) That Regulates Intestinal, Transport, Proceedings of the National Academy of Sciences of USA, national Academy of Science, vol. 95, Jun. 1998, pp. 7766-7771.
Langguth, P., et al., The Challenge of Proteolytic Enzymes in Intestinal Peptide Delivery, Journal of Controlled Release, Elsevier Science Publishers B.V. Amsterdam, NL, vol. 46, No. 1, May 1997, pp. 39-57.
Egleton, R.D., et al., Improved Bioavailability to the Brain of Glycosylated Mat-Enkephalin Analogs, Brain Research, vol. 881, No. 1, 2000, pp. 37-46.

(Continued)

*Primary Examiner* — Cecilia Tsang
*Assistant Examiner* — Roy Teller
(74) *Attorney, Agent, or Firm* — McCarter & English, LLP

(57) ABSTRACT

Pharmaceutical agents, compositions containing the same and methods for their use for enhancing the bioavailability and pharmacological efficacy of therapeutic peptides. The pharmaceutical agents have the formula Carrier-Linker-Peptide Wherein Peptide is a therapeutically active peptide species having the formula $aa_n$ wherein n is the number of amino acid residues in the peptide and n is 2 to 40, Carrier is benzoyl, phenylacetyl, cinnamoyl, 3-OH-cinnamoyl, 3,4-OH-cinnamoyl, 3,4-dimethoxycinnamoyl, 3,4-methylenedioxycinnamoyl, 3-methoxycinnamoyl, 3,4-diethoxy-cinnamoyl, 3,4,5-trimethoxy-cinnamoyl, t-butoxycarbonyl, benzyloxycarbonyl, pivaloyl, N-9-fluorenylmethoxycarbonyl, fumaroyl and derivatives thereof and Linker is a C6 to C16 lipidic chain or a derivative thereof, an 8-amino-3,6-dioxaoctanoic acid or polymeric derivative thereof, pseudo peptide, or peptide mimic. Methods of use of compositions having the formula Carrier-Peptide wherein Carrier and Peptide are as just defined are also disclosed.

14 Claims, No Drawings

OTHER PUBLICATIONS

Pauletti, G.M., et al., Improvement of Oral Peptide Bioavailability: Peptidomimetics and Prodrug Strategies, Advanced Drug Delivery Review, vol. 27, No. 203, 1997, pp. 235-256.
Ahlers, et al., Enhanced Immunogenicity of HIV-1 Vaccine Construct by Modification of the Native Peptide Sequence, Proc. Natl. Acad. Sci. USA, vol. 94, pp. 10856-10861, Sep. 1997.
Greenstein, et al., A Universal T Cell Epitope-Containing Peptide From Hepatitis B Surface Antigen Can Enhance Antibody Specific for HIV gp120, Journal of Immunology, vol. 148, pp. 3970-3977, No. 12, Jun. 1992.
Belyakov, et al., The Importance of Local Mucosal HIV-Specific CD8* Cytotoxic T Lymphocytes for Resistance to Mucosal Viral Transmission in Mice and Enhancement of Resistance by Local Administration of IL-12, The Journal of Clinical Investigation, vol. 102(12); pp. 2072-2081, Dec. 1998.
Belyakov, et al., Mucosal Immunization With HIV-1 Peptide Vaccine Induces Mucosal and Systemic Cytotoxic T Lymphocytes and Protective Immunity in Mice Against Intrarectal Recombinant HIV_ Vaccinia Challenge, Proc. Natl. Acad. Sci. USA, vol. 95, pp. 1709-1714, Feb. 1998.
Patel, et al., Oral Administration of Insulin by Encapsulation within Liposomes, North-Holland Publishing Company, vol. 62, No. 1, pp. 60-63, Feb. 1976.
Hashimoto, et al., ACTH Release in Pituitary Cell Cultures, Effect of Neurogenetic Peptides and Neurotransmitter Substances Corticotropin Releasing Factor (CRF), Endocrinol. Japan, vol. 26(1), pp. 103-109, Feb. 1979.
Bernatowicz et al., Development of Potent Thrombin Receptor Antagonist peptides, *J. Med. Chem.* 1996, 39:4879-87.
U.S. Appl. No. 09/844,426, filed Aug. 7, 2000.

COMPOSITIONS AND METHODS FOR ENHANCED PHARMACOLOGICAL ACTIVITY OF COMPOSITIONS COMPRISING PEPTIDE DRUG SUBSTANCES

REFERENCE TO RELATED APPLICATIONS

This application is a divisional application of U.S. patent application Ser. No. 10/825,472 filed Apr. 15, 2004, now U.S. Pat. No. 7,671,029; which is a continuation-consolidation of application Ser. No. 09/844,426 filed Aug. 7, 2000, now abandoned; Ser. No. 10/050,903 filed Jan. 16, 2002, now U.S. Pat. No. 6,908,900; and Ser. No. 10/237,254 filed Sep. 6, 2002, now abandoned. This application claims benefit under Title 35, U.S.C. §119(e), of U.S. Application Ser. Nos. 60/147,749 filed Aug. 6, 1999; 60/317,737, filed Sep. 6, 2001; 60/262,337, filed Jan. 17, 2001; 60/332,636, filed Nov. 6, 2001; 60/287,872, filed May 1, 2001; and 60/287,886, filed May 1, 2001.

INCORPORATION BY REFERENCE

The present specification incorporates by reference the Computer Readable Form of the Sequence Listing filed on Feb. 8, 2011, file name: 101448_00062_ST25.txt; size 4 KB; created on: Feb. 8, 2011; using PatentIn-3.5 software.

FIELD OF THE INVENTION

This invention, in general, relates to compositions and methods that permit oral and parenteral administration, and significantly enhance the bioavailability and pharmacological effects of therapeutically active peptides, pseudo-peptides and peptide mimics, particularly those that are otherwise poorly orally absorbable or display only minimal bioavailability if administered parenterally.

BACKGROUND OF THE INVENTION

It has been reported in the literature that therapeutically effective peptides ($aa_n$) with two or more amino acids ($n \geqq 2$) are poorly absorbed orally. Even a peptide of as few as two amino acids, or related structures, exhibits very narrow absorption windows and poor bioavailability. As an example, the Physician's Desk Reference (PDR) reports that the angiotensin converting enzyme (ACE) inhibitor Enalaprilat ($R_1$-Ala-Pro; n=2) is very poorly absorbed orally. Enalapril ($R_2$-Ala-Pro), which is a pro-drug of Enalaprilat, is better absorbed orally, but the end result demonstrates only a 25% relative bioavailability of the active moiety (Enalaprilat) released from in vivo cleavage of the pro-drug. In comparison, Lisinopril ($R_3$-Lys-Pro) has relatively good solubility in water, but only a moderate oral bioavailability (<25%), with a $T_{max}$ (time to maximum serum levels in vivo) of more than seven hours. Thus, this class of therapeutic species is preferably administered via a non-oral delivery method, such as by injection. However, even when delivered intravenously, the therapeutically active species has a relatively short serum half-life.

It is also known that some tri-peptides originating in food products may be capable of effective oral absorption, but to an unknown extent. However, no active tri- or longer peptide drug substances ($n \geqq 3$) displaying oral absorption have been identified.

In accordance with the present invention compositions and methods providing for the oral absorption of peptide drug substances ($aa_n$) and other poorly orally absorbed drugs are disclosed. Furthermore, it has now been found that, through practice of the methods of the present invention, the length of the peptide drug entity (n) can be increased, particularly when the composition is administered parenterally, such as by intravenous (i.v.) administration, with the result of significantly improved pharmacological and therapeutic effects for the active drug moiety. Accordingly, through the practice of the present invention, it is possible to chemically modify a peptide species a pseudo-peptide or peptide mimic of known therapeutic utility to both permit the oral administration of the species and to drastically improve its pharmacological properties even when administered through a parenteral route. The invention also makes it possible to provide a cellular immune response in immunizing against agents such as viruses for which antibodies have been shown to enhance infectivity and in providing such a response against both chronic and latent viral infections and against malignant cells.

In the present disclosure, the word "peptide" corresponds to any sequence of naturally occurring amino acids, as well as to pseudo-peptides and to peptide mimics. By "pseudo-peptide," is meant a chemical modification of one or more of the amino acid residues constituting the peptide or of their bonds such as, but not limited to, use of amino acids in their D-configuration, use of N-methyl amino acids, replacement of one or more peptidic bonds (—CO—NH) by a reduced bond (—$CH_2NH$) and/or by —NHCO, —$CH_2CH_2$, —$COCH_2$, —$CHOHCH_2$ or —CH2O. By "peptide mimic," is meant any amino acid sequence in which the —C— backbone has been replaced by an oligourea backbone or an oligocarbamate backbone. ω-Peptides are also included in this definition.

By "lipopeptides" is meant a combination of natural peptides (not involving any modified amino acids or modified bonds) and a lipid moiety;

By "lipopseudo-peptides" is meant pseudo-peptides coupled with a lipid moiety.

By "chemically modified amino acid $aa_n$," is meant an amino acid sequence wherein at least one of the amino acid residues in their bonds is modified as set forth above in these definitions.

SUMMARY OF THE INVENTION

The instant invention is directed to pharmaceutical agents having the formula Carrier-$Linker_x$-Peptide Wherein X is 0 or 1, Carrier is selected from benzoyl, phenylacetyl, cinnamoyl, 3-OH-cinnamoyl, 3,4-OH-cinnamoyl, 3,4-methylenedioxycinnamoyl, 3-methoxycinnamoyl, 3,4-dimethoxy-cinnamoyl, 3,4,5-trimethoxycinnamoyl, t-butoxycarbonyl, benzoyloxycarbonyl, pivaloyl, N9-fluorenyl methoxycarbonyl, fumaroyl and derivatives thereof; Peptide is a therapeutically active peptide species $aa_n$ wherein n is the number of amino acid residues in the peptide and is an integer of 2 to 40 and Linker is selected from C6 to C16 lipidic chains and derivatives thereof, 8-amino-3,6-dioxaoctanoic acid and polymeric derivatives thereof, pseudopeptides and peptide mimics. The invention is further directed to pharmaceutical compositions containing the afore-identified pharmaceutical agents as active ingredients and to methods of making and using the same.

In an embodiment of the invention, Carrier or Carrier-Linker is bound to a free NH2 function of the peptide and preferably to the NH2 function of the N-terminal amino acid of the peptide.

Carrier is selected from a group consisting of Cinnamoyl, 3-OH-Cinnamoyl, 3,4-OH-Cinnamoyl, 3,4-methylenedioxycinnamoyl, 3-methoxycinnamoyl, 3-4-dimethoxycinnamoyl, 3,4,5-trimethoxy-cinnamoyl and derivatives thereof, and Peptide is a therapeutically active peptide species and is in the form $aa_n$, where n is the number of amino acid residues in the peptide and wherein n is an integer from 2 to 40.

In an embodiment, the present invention provides a pharmaceutical agent comprising a carrier moiety and a therapeutically active peptide species, wherein the peptide is in the form $aa_n$, where n is the number of amino acid residues in the peptide. Preferably, the carrier moiety comprises an aryl or alkyl group of sufficient length or steric bulk to protect the active peptide species from enzymatic degradation in vivo. More preferably, the carrier is selected from a group comprising cinnamoyl, benzoyl, phenylacetyl, 3-OH-cinnamoyl, 3,4-OH-cinnamoyl, 3,4-methylenedioxycinnamoyl, 3-methoxycinnamoyl, 3,4-dimethoxycinnamoyl, 3,4,5-trimethoxycinnamoyl, t-butoxycarbonyl, benzyloxycarbonyl, pivaloyl, N-9-fluorenylmethoxycarbonyl, and fumaroyl. Furthermore the carrier moiety can be chemically linked to a therapeutically active peptide species of the general formula $aa_n$, where n is an integer from 2 to 40. In addition, this embodiment of the present invention contemplates a therapeutically active peptide species that is poorly absorbed orally. Preferably, n is an integer from 3 to 6. More preferably, n is 5. More preferably still, the therapeutically active peptide species comprises Tyr-Gly-Gly-Phe-Met (SEQ ID NO: 1).

In an alternative embodiment, the pharmaceutical agent of the present invention further comprises a linker species linking the peptide to the carrier moiety. Preferably, the linker species is selected from the group consisting of a natural peptide, a pseudo-peptide, and a peptide mimic, each member of the group comprising 4 or fewer amino acid residues. In one aspect of this embodiment of the present invention, the linker species is directly bound to the carrier. Alternatively, the linker species is bound to the carrier through a —$C_6$ or —$C_8$ acidic moiety. More preferably, the linker species is Gly-carba-Gly, a pseudo-peptide. As used herein Gly-carba-Gly represents a di pseudo-peptide constructed with two glycines, i.e., G·($CH_2$—$CH_2$)G. $G_{95}$·($CH_2$—$CH_2$)$G_{96}$ represents a pseudo-peptide link between two glycines in positions 95 and 96 of the nef peptide. More preferably still, the linker species is associated with a —$C_n$ chain, where n is an integer from 6 to 8. The linker species is bound to a free $NH_2$ function of the peptide, preferably to the N-terminal amino acid of the peptide.

Preferably, the therapeutically active peptide species comprises Tyr-Gly-Gly-Phe-Met (SEQ ID NO:1).

In an alternative embodiment, the pharmaceutical agent of the present invention further comprises a linker species linking the peptide to the carrier moiety wherein the linker species is selected from a group comprising a C6 to C16 lipidic chain and derivatives thereof, 8-amino-3,6-dioxa octanoïc acid and polymeric derivatives thereof, a pseudo-peptide or a peptide mimic of less than 4 residues and any combination thereof.

In yet another embodiment, the present invention contemplates a method for the treatment of a physiological condition through administration of a therapeutically effective species comprising the steps of chemically linking a therapeutic peptide of the general formula $aa_n$, where aa is an amino acid, and where n is an integer from 2 to 40, to an alkyl or aryl carrier moiety to form a pro-drug, and administering the pro-drug to a patient exhibiting the physiological condition. Preferably, the therapeutic peptide used in the practice of the invention is poorly absorbed orally, and the carrier moiety is selected from the group comprising cinnamoyl, benzoyl, phenylacetyl, 3-OH-cinnamoyl, 3,4-OH-cinnamoyl, 3-methoxy-cinnamoyl, 3,4-methylenedioxycinnamoyl, 3,4,5-trimethoxycinnamoyl, t-butoxycarbonyl, benzyloxycarbonyl, pivaloyl, N-9-fluorenylmethoxy-carbonyl, and fumaroyl.

Alternatively, this embodiment of the present invention provides a method wherein the pro-drug is administered orally or parenterally. In yet another alternative of the present embodiment, the method contemplates the use of a therapeutic peptide that is chemically linked to the carrier moiety through a linker species.

In still another alternative embodiment, the present invention provides a method to enhance the absorption and bioavailability of an active peptide drug substance of the form $aa_n$ in a pharmaceutical formulation, the method comprising the steps of adding a peptide moiety $X_n$, where n=1-3, and where a terminal amino acid is selected from the group consisting of Pro, Met and Arg, to one end of the peptide drug substance, and adding a protecting moiety to the opposite end of the peptide drug substance.

Alternatively, the invention of the instant application provides a method to enhance the absorption and bioavailability of an active peptide drug substance of the form $aa_n$ in a pharmaceutical formulation, the method comprising the step of formulating the active peptide drug substance with a terminal amino acid selected from the group consisting of Pro, Met and Arg, and with a protective moiety on the opposite terminus of the peptide substance, wherein the terminal amino acid (Pro, Met or Arg) is not blocked by the protective moiety.

In one embodiment, the present invention provides a pharmaceutical composition for use in the treatment of physiological conditions comprising a carrier moiety and a therapeutically active peptide species as defined above. The carrier comprises an aryl or alkyl group of sufficient length and/or steric bulk to inhibit rapid enzymatic degradation of the active drug species in vivo. A preferred carrier is selected from a group comprising cinnamoyl, benzoyl, phenylacetyl, 3,4-methylenedioxycinnamoyl, 3,4,5-trimethoxy-cinnamoyl, t-butoxycarbonyl, benzyloxycarbonyl, pivaloyl, N-9-fluorenylmethoxycarbonyl, and fumaroyl. The carrier moiety is chemically linked to a therapeutic peptide of the general formula $aa_n$, where aa is an amino acid, or a chemical or structural variation thereof as defined above, where n is an integer from 2 to 40, and wherein the peptide is poorly absorbed orally. Preferably, in the drug composition of the invention, n is an integer from 3 to 6. More preferably, n is 5. In a particularly preferred embodiment, the peptide is Tyr-Gly-Gly-Phe-Met (SEQ ID NO: 1).[1]

[1] Try=Tyrosine; Gly=Glysine; Phe=Phenylalanine; Met=Methionine.

In another embodiment, the present invention provides a pharmaceutical composition for administration to a patient in need thereof comprising the pharmaceutical agent described immediately above, and one or more pharmaceutically acceptable adjuvants. Preferably, the composition is formulated for oral administration. Alternatively, the composition is formulated for parenteral or topical administration. The composition is advantageously formulated for intravenous administration. This embodiment of the present invention also contemplates a composition that releases a biologically active form of the pharmaceutical agent into the patient's system at physiologically effective levels over a period of time of up to twelve hours. Most preferably, the composition releases a biologically active form of the pharmaceutical agent into the patient's system at physiologically effective levels over a period of time of up to twenty-four hours. In this embodiment of the present invention, the peptide species is preferably an epitope or an immune sequence characteristic of an infectious, viral or cancerous disease.

When delivered orally, the drug composition of the present invention is capable of delivering a systemic dose of the active drug species to a patient ingesting the pro-drug. The active peptide, normally immediately degraded in the gastrointestinal tract to non-therapeutic forms, survives due to the protective effect of the carrier component, and persists in the patient's system for prolonged periods of time. Over time, the multi-component system is slowly broken down, probably by enzymatic hydrolysis in the liver or the plasma, releasing the pharmacologically active component. An added benefit of the present invention is that the kinetics of such breakdown to release the active component are significantly slower than for the processes associated with metabolic breakdown of the unmodified peptide drug species, effectively permitting a sustained, controlled release of the active species into the patient's system, thus maintaining pharmacologically effective blood serum levels over an extended period of time.

In another embodiment, the present invention contemplates a pharmaceutical composition comprising a similar multi-component entity which, when administered through a parenteral route, makes use of protective activity towards the enzymatic breakdown provided by association of the active drug species with the carrier and/or linking components, increasing thereby the in vivo half-life of the therapeutic component and improving its pharmacological properties. A preferred therapeutic moiety for use in this embodiment of the present invention is an epitope or an immune sequence characteristic of an infectious, viral or cancerous disease. This invention, therefore, provides a delivery method for such immune competent peptides that enhances their pharmacological efficacy.

As would be recognized by one of skill in the art, one or more of the amino acids of the therapeutically active peptides used in conjunction with the present invention may be modified chemically or conformationally without significantly diminishing, and preferably enhancing, the pharmacological activity of the therapeutic entity. These modified peptides may be used in the practice of the present invention.

Ideally, the composition of the present invention is formulated into a pharmaceutical composition with pharmaceutically acceptable adjuvants known to those of skill in the art of pharmaceutical formulation chemistry.

Known therapeutically active peptide species that have been demonstrated to be pharmacologically ineffective when delivered through typical oral routes of administration can be modified through linkage to a carrier species to achieve effective bioavailability of the active entity, as well as therapeutically effective controlled release of the active species.

By, utilizing the present invention, it is now possible to treat physiological conditions through oral administration of therapeutically active peptides that would normally have to be administered through considerably less desirable routes of administra-tion or with less effectiveness.

EXAMPLES

Met-Enkephalin (Tyr-Gly-Gly-Phe-Met*) (SEQ ID NO:1) hereinafter (YGGFM) is a naturally occurring pentapeptide (n=5) belonging to the endorphin class. It is known to be involved in the basic mechanisms of analgesia. It produces a transient analgesic effect when administered parenterally, but no effect has been observed when given orally. Its mechanism of action is believed to involve binding to opioid delta receptors in the brain. Met-Enkephalin is very rapidly degraded in vivo into a tetra-peptide that is subsequently metabolized. As for the pharmacokinetics of Met-Enkephalin, the plasma levels of the pro-drug, as well of those of the metabolites, are barely measurable, even when administered parenterally.

Example 1

Analgesic Effects from Administration of CY5M, a Cinnamoyl-Met-Enkephalin (SEQ ID NO:1) Pro-Drug of the Present Invention According to the present invention, a pro-drug, designated CY5M for convenience of reference, comprising cinnamoyl-Met-Enkephalin (cinnamoyl-YGGFM), having the general forming carrier-$aa_5$, demonstrated an unexpectedly strong, long-lasting analgesia in a hot plate test with rats both when administered orally, and when administered parenterally.

Methods and Materials

Analgesic activity is classically demonstrated using a hot plate test using rats as test animals. The time to first licking of the posterior foot by the rat is recorded after the rat has been place on a hot plate maintained at an elevated temperature (40° C.). This procedure provides accurate data on central analgesic activities induced by various candidate drugs. Under placebo conditions, the time to first licking of the posterior foot of the test animal varies between 30 and 50 seconds. A marked analgesia is demonstrated when this time is more than doubled. In the experiments reported herein, a standard hot plate test was used to assess analgesia and the time to first licking of the test animal's posterior foot was used as the triggering event for measurement of elapsed time as indicative of the pharmacological effect of the administered drug species.

Seven groups of five male Wistar rats each were randomly assigned to the following treatments: placebo, 1 mg/kg morphine (i.v.), 10 mg/kg morphine (oral), 10 mg/kg codeine (oral), 10 mg/kg ibuprofen (oral), 2.5 mg/kg CY5M (i.v.), and 2.5 mg/kg CY5M (oral). The method was pre-validated with two oral and i.v. administrations of saline placebo and the results were similar to those obtained with placebo in the experiment reported below.

Results

TABLE 1

| Time to first signal activity after oral administration | | | | | | |
|---|---|---|---|---|---|---|
| Placebo | 53.2 | 30.6 | 38.4 | 45.0 | 46.6 | 42.0 |
| Morphine | 51.8 | 84.8 | 81.2 | 58.8 | 48.8 | 42.0 |
| Codeine | 53.2 | 51.4 | 64.6 | 57.6 | 56.2 | 46.4 |
| Ibuprofen | 53.2 | 55.0 | 70.4 | 66.0 | 54.0 | 44.2 |
| CY5M | 53.6 | 46.2 | 78.8 | 78.2 | 82.6 | 98.8 |

TABLE 2

| Time to first signal activity after i.v. administration | | | | | | |
|---|---|---|---|---|---|---|
| | Time | | | | | |
| | 0 h | 1 h | 2 h | 4 h | 6 h | 24 h |
| Placebo | 53.2 | 30.6 | 38.4 | 45.0 | 46.6 | 42.0 |
| morphine | 51.8 | 118.8 | 86.6 | 63.2 | 45.6 | 40.0 |
| CY5M | 51.0 | 57.0 | 114.0 | 88.2 | 106.0 | 86.6 |

In a preliminary study (data not shown), Met-Enkephalin alone was unable to demonstrate any effect after oral administration at a 5 mg/kg dose, whereas a transient effect of about 15 minutes was observed after i.v. administration.

If the area under the dose response curve is taken as a rough estimate of the average effect, the results indicate that 1 mg/kg morphine i.v. is comparable to 10 mg/kg morphine oral. In comparison, CY5M, administered either orally or by i.v., is at least 8 times more effective than morphine using the same route of administration. Of further interest, the above data also indicate that in no case did morphine exhibit an analgesic effect lasting longer than six hours, whereas both oral and i.v. administrations of CY5M demonstrated a significant analgesic effect for a period of time of 24 hours or longer.

These results indicate that using a carrier such as disclosed herein in association with a peptide drug species, permits the effective oral absorption of peptides of at least 5 amino acids in length and allows a much stronger pharmacological effect, with significantly enhanced pharmacokinetic profiles, by both oral and i.v. routes of administration. Analogs of CY5M comprising a linker species in addition to the cinnamoyl carrier species, will demonstrate similar or greater effects than those provided above.

Example 2

A Series of Carrier-Linker-Peptides Having the Formula Carrier-(Linker)-Peptide was Tested in their Ability to Induce T Cell Proliferation in a Skin Immunization Model Model:

9 week old mice were immunized by application on bare skin of 100·g of Nef$_{(66\text{-}97)}$ peptide sequence and modifications thereof in addition to 5·g of choleric toxin and 100·g of oligodeoxynucleotide containing a CpG moiety (Immunology, 2002 104:1-14). 2 weeks later splenocytes were collected and grown over 4 days in the presence of 4 different concentrations of Nef$_{(66\text{-}97)}$ peptide (SEQ ID NO:2). The proliferation was measured by incorporating tritiated thymidine.

Formulations

```
Nef = Nef(66-97):
VGFPVTPQVPLRPMTYKAAVDLSHFLKEKGGL   (SEQ ID NO: 2)
```

Lipo=Nef$_{(66\text{-}97)}$-palmitoyl lysilamide

C0=Cinnamoyl-Nef$_{(66\text{-}97)}$ $G_{95}\psi$ . . . ($CH_2$—$CH_2$) $G_{96}$

CC5=Cinnamoyl-aminovaleryl-Nef$_{(66\text{-}97)}$ $G_{95}\psi$ . . . ($CH_2$—$CH_2$) $G_{96}$ CC8=Cinnamoyl-aminooctanoyl-Nef$_{(66\text{-}97)}$ $G_{95}\psi$ . . . ($CH_2$—$CH_2$) $G_{96}$ Pivgal=D-Gal$(OPiv)_4$-hydroxyvaleryl-aminooctanoyl-Nef$_{(66\text{-}97)}$ $G_{95}\psi$ . . . ($CH_2$—$CH_2$) $G_{96}$ where $G_{95}\psi$ . . . ($CH_2$—$CH_2$) $G_{96}$ represents the pseudo-peptide chemical modification of $G_{95\ .\ .\ .\ 96}G$ of the Nef$_{(66\text{-}97)}$ sequence (SEQ ID NO:2).

Results: Proliferation Index

| Conc. of Nef peptide: | Nef | Lipo | C0 | CC5 | CC8 | Pivgal |
|---|---|---|---|---|---|---|
| 50 | 10 | 07 | 12 | 20 | 16 | 10 |
| 5 | 13 | 08 | 14 | 21 | 20 | 08 |
| 0.5 | 10 | 06 | 12 | 22 | 22 | 05 |
| .05 | 03 | 03 | 08 | 11 | 10 | 02 |

The results clearly show that CC5 and CC8 have the best proliferation index. The addition to the Cinnamoyl carrier of a covalently bound linker (Cinnamoyl+fatty acid in C5 or C8) is required to enhance the activity compared to the baseline. Peptides without the carrier of the present invention=peptide+C16 fatty acid (hexadecanoic acid derivative) are not as effective. Derivatives using Pivaloyl carrier did not demonstrate improved activity. Cinnamoyl alone showed a trend to improved activity.

The results reported above clearly demonstrate that in certain circumstances the use of an additional linker may be critical and depends upon the peptide sequence (Nef$_{(66\text{-}97)}$ (SEQ ID NO:2) compared to YGGFM (SEQ ID NO:1)) and the therapeutic effect: (pharmacologically active peptide (YGGFM) compared to immune competent peptide (Nef$_{(66\text{-}97)}$).

The pro-drugs of the present invention are formulated into pharmaceutical compositions that contain an efficacious amount of at least one lipopseudo-peptide in combination with an inert pharmaceutical vehicle.

The pharmaceutical compositions contain the derivatives alone or in combination with other medications.

The pharmaceutical compositions of the invention can be administered in different forms and by different routes, namely nasal, rectal and oral and by injection.

In the case of administration by the oral route, they may be used in the form of tablets, pills, lozenges, gelatin capsules and even liposomes. These compositions advantageously contain from 0.05·g to 100 mg of lipo-pseudo peptide, per dosage unit.

The pseudo-peptides of the invention are particularly useful in improving the immune response against agents such as viruses for which antibodies have been shown to enhance infectivity, particularly to provide such a response against Goth chronic and latent viral infectious and malignant cells.

The present invention also provides a method for enhancing the oral availability of therapeutic pseudo-peptides of the formula $aa_n$, where aa is a chemically modified amino acid, or a chemical or structural variation thereof, where n is an integer of from 2 to 40, and wherein the pseudo-peptide is poorly absorbed orally, wherein the method comprises the step of chemically linking the pseudo-peptide to a carrier moiety selected from the group including cinnamoyl, benzoyl, phenylacetyl, 3-OH-cinnamoyl, 3,4-OH-cinnamoyl, 3,4-methylenedioxycinnamoyl, 3-methoxycinnamoyl, 3,4-dimethoxycinnamoyl, and 3,4,5-trimethoxycinnamoyl to form a pro-drug. Preferably, this embodiment of the present invention provides a pro-drug where the pseudo-peptide is chemically linked to the carrier moiety through a non-therapeutic linker species. More preferably, the linker species is an amino acid.

The instant invention also encompasses a method for the treatment of a physiological condition through the oral administration of a therapeutically effective species comprising the steps of chemically linking a therapeutic pseudo-peptide of the formula $aa_n$, where aa is a chemically modified amino acid, or a chemical or structural variation thereof, where n is an integer from 2 to 40, and wherein the pseudo-peptide is poorly absorbed orally, to a carrier moiety selected from the group including cinnamoyl, benzoyl, phenylacetyl, 3-OH-cinnamoyl, 3,4-OH-cinnamoyl,3,4-methylene-dioxy-cinnamoyl 3-methoxycinnamoyl, 3,4-dimethoxycinnamoyl and 3,4,5-trimethoxycinnamoyl to form a pro-drug, and orally administering the pro-drug to a patient exhibiting the physiological condition. Preferably, in the practice of the method of the present invention, the peptide is chemically linked to the carrier moiety through a non-therapeutic linker species. More preferably still, the linker species is an amino acid.

Thus, utilizing the present invention, it is possible to treat physiological conditions through oral administration of therapeutically active pseudo-peptides that would normally have to be administered through considerably less desirable routes of administration, such as by injection.

In still another embodiment, the invention of the instant application provides for a method for the controlled release administration of a therapeutically effective pseudo-peptide of the formula $aa_n$, where aa is a chemically modified amino acid, or a chemical or structural variation thereof, where n is an integer from 2 to 40, and wherein the pseudo-peptide is poorly absorbed orally, comprising the steps of chemically linking the peptide to a carrier moiety selected from the group comprising cinnamoyl, benzoyl, phenylacetyl, 3-OH-cinnamoyl, 3,4-OH-cinnamoyl, 3-methoxy-cinnamoyl, 3,4-dimethoxycinnamoyl, 3,4-methylenedioxycinnamoyl and 3,4,5-trimethoxycinnamoyl to form a pro-drug, and orally administering the pro-drug to a patient. In a preferred embodiment, the pseudo-peptide is chemically linked to the carrier moiety through a non-therapeutic linker species, and, more preferably still, the linker species is an amino acid. Due to the kinetics of the hepatic degradation of the pro-drug of the present invention, the therapeutically active peptide species is released to the patient's system over relatively long periods of time, dosage dependent, to a maximum of nearly twenty-four hours.

What is claimed is:

1. A method of significantly enhancing the bioavailability of pharmaceutical effects of therapeutically active peptides comprising:

orally or parentally administering to a patient an effective amount of a pharmaceutical composition comprising a pharmaceutically acceptable adjuvant and a pharmaceutical agent having the general formula:

Carrier-Linker-Peptide;

wherein Peptide is a therapeutically active peptide of from 2 to 40 amino acids;

wherein Carrier comprises an aryl or alkyl group of sufficient length or steric bulk to inhibit rapid enzymatic degradation of the therapeutically active peptide species and is a member selected from the group consisting of cinnamoyl, benzoyl, phenylacetyl, 3-OH-cinnamoyl, 3,4-OH-cinnamoyl, 3,4-methylenedioxycinnamoyl, 3-methoxycinnamoyl, 3,4-dimethoxycinnamoyl, 3,4,5-trimethoxy-cinnamoyl, t-butoxy-carbonyl, benzyloxycarbonyl, pivaloyl, N-9-fluorenylethoxycarbonyl, fumaroyl, and combinations thereof; and Linker is a member selected from the group consisting of C5 to C16 lipidic chains, 8-amino-3,6-dioxaoctanoic acid, a peptide of less than 4 residues, and combinations thereof; and wherein the pharmaceutical composition is more biologically and/or pharmacologically efficacious compared to administration of the Peptide therapeutically active alone.

2. The method of claim 1, wherein the Peptide alone is poorly absorbed orally.

3. The method according to claim 1, wherein the pharmaceutical composition is administered orally or parenterally.

4. The method of claim 1, wherein the pharmacological effect comprises providing a cellular immune response.

5. The method of claim 1, wherein the pharmacological effect is analgesia.

6. The method of claim 1, wherein the Peptide is met-enkephalin peptide (SEQ ID NO:1).

7. The method of claim 1, wherein the Peptide is a $Nef_{(66-97)}$ peptide (SEQ ID NO:2).

8. The method of claim 1, wherein the pharmaceutical composition releases a biologically active form of the pharmaceutical agent into the patient's system at physiologically effective levels over a period of up to twelve hours.

9. The method of claim 1, wherein the pharmaceutical composition releases a biologically active form of the pharmaceutical agent into the patient's system at physiologically effective levels over a period of up to twenty-four hours.

10. The method of claim 6, wherein the pharmaceutical agent is administered at a dose of 2.5 mg/kg.

11. A method for modifying a peptide drug substance comprising the steps of: adding a peptide moiety of the general formula Xn to one terminus of the peptide, wherein n is an integer of from 1 to 3, and X is an amino acid selected from the group consisting of Proline, Methionine, and Arginine; and adding a protecting moiety to the other terminus of the peptide, wherein the modified peptide demonstrates enhanced absorption or bioavailability or both compared to an unmodified peptide.

12. The method of claim 11, wherein the protecting moiety is selected from the group consisting of cinnamoyl and benzyl, and the terminal amino acid is not blocked by the protective group.

13. The method of claim 11, wherein the modified peptide is combined with a pharmaceutically acceptable adjuvant.

14. A method of treating a physiologic condition comprising administering to a patient an effective amount of a peptide modified as in claim 11 together with a pharmaceutically acceptable adjuvant.

* * * * *

```
                              SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(5)
<223> OTHER INFORMATION: Met-Enkephalin

<400> SEQUENCE: 1

Tyr Gly Gly Phe Met
1               5


<210> SEQ ID NO 2
<211> LENGTH: 32
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(32)
<223> OTHER INFORMATION: Nef(66-97) Peptide

<400> SEQUENCE: 2

Val Gly Phe Pro Val Thr Pro Gln Val Pro Leu Arg Pro Met Thr Tyr
1               5                   10                  15

Lys Ala Ala Val Asp Leu Ser His Phe Leu Lys Glu Lys Gly Gly Leu
            20                  25                  30
```